(12) United States Patent
Lomholt

(10) Patent No.: US 6,651,664 B1
(45) Date of Patent: Nov. 25, 2003

(54) TRACHEAL TUBE WITH BULGED CUFF

(76) Inventor: Niels Lomholt, 4 Lars Nielsens Vej, Hørsholm (DK), DK-2970

( * ) Notice: Subject to any disclaimer, the term of this patent is extended or adjusted under 35 U.S.C. 154(b) by 0 days.

(21) Appl. No.: 09/958,190

(22) PCT Filed: Apr. 12, 2000

(86) PCT No.: PCT/DK00/00178

§ 371 (c)(1),
(2), (4) Date: Oct. 3, 2001

(87) PCT Pub. No.: WO00/62849

PCT Pub. Date: Oct. 26, 2000

(30) Foreign Application Priority Data

Apr. 20, 1999 (DK) .......................... 1999 00530

(51) Int. Cl.⁷ ............................................. A61M 16/00
(52) U.S. Cl. ............................ 128/207.14; 128/200.26
(58) Field of Search .................. 128/207.14, 207.15, 128/200.26, 207.29; 604/96.01, 103.08, 103.06

(56) References Cited

U.S. PATENT DOCUMENTS

| | | | | | |
|---|---|---|---|---|---|
| 3,659,611 | A | * | 5/1972 | Miller | 128/207.15 |
| 3,810,474 | A | * | 5/1974 | Cross | 128/207.15 |
| 4,340,046 | A | * | 7/1982 | Cox | 128/207.17 |
| 5,207,700 | A | * | 5/1993 | Euteneuer | 606/194 |
| 5,494,029 | A | * | 2/1996 | Lane et al. | 128/207.15 |
| 5,520,175 | A | * | 5/1996 | Fry | 128/207.15 |
| 5,765,559 | A | * | 6/1998 | Kim | 128/207.15 |
| 5,819,733 | A | * | 10/1998 | Bertram | 128/207.15 |

FOREIGN PATENT DOCUMENTS

| | | | |
|---|---|---|---|
| DE | 3519626 | * | 12/1986 |
| WO | WO 95/09665 | * | 4/1995 |

* cited by examiner

Primary Examiner—Weilun Lo
Assistant Examiner—Mital Patel
(74) Attorney, Agent, or Firm—Merchant & Gould, P.C.

(57) ABSTRACT

The invention concerns a tracheal tube with an inflatable cuff surrounding the tube which has a sealing function against the trachea, and which is through a separate channel connected to the surroundings to monitor and regulate the inside pressure in the inflated cuff. The particular feature of the inflatable cuff is a number of local bulges distributed along the circumference of the cuff. With the invention it is accomplished that the sealing in the areas with bulges becomes effective, because the channels formed by the length-wise folds in the cuff are interrupted by thin-walled bulges, in such a way that liquid and secretions do not penetrate down into the patient's lungs.

7 Claims, 2 Drawing Sheets

TRACHEAL TUBE WITH BULGED CUFF

Figures 1, 1A:
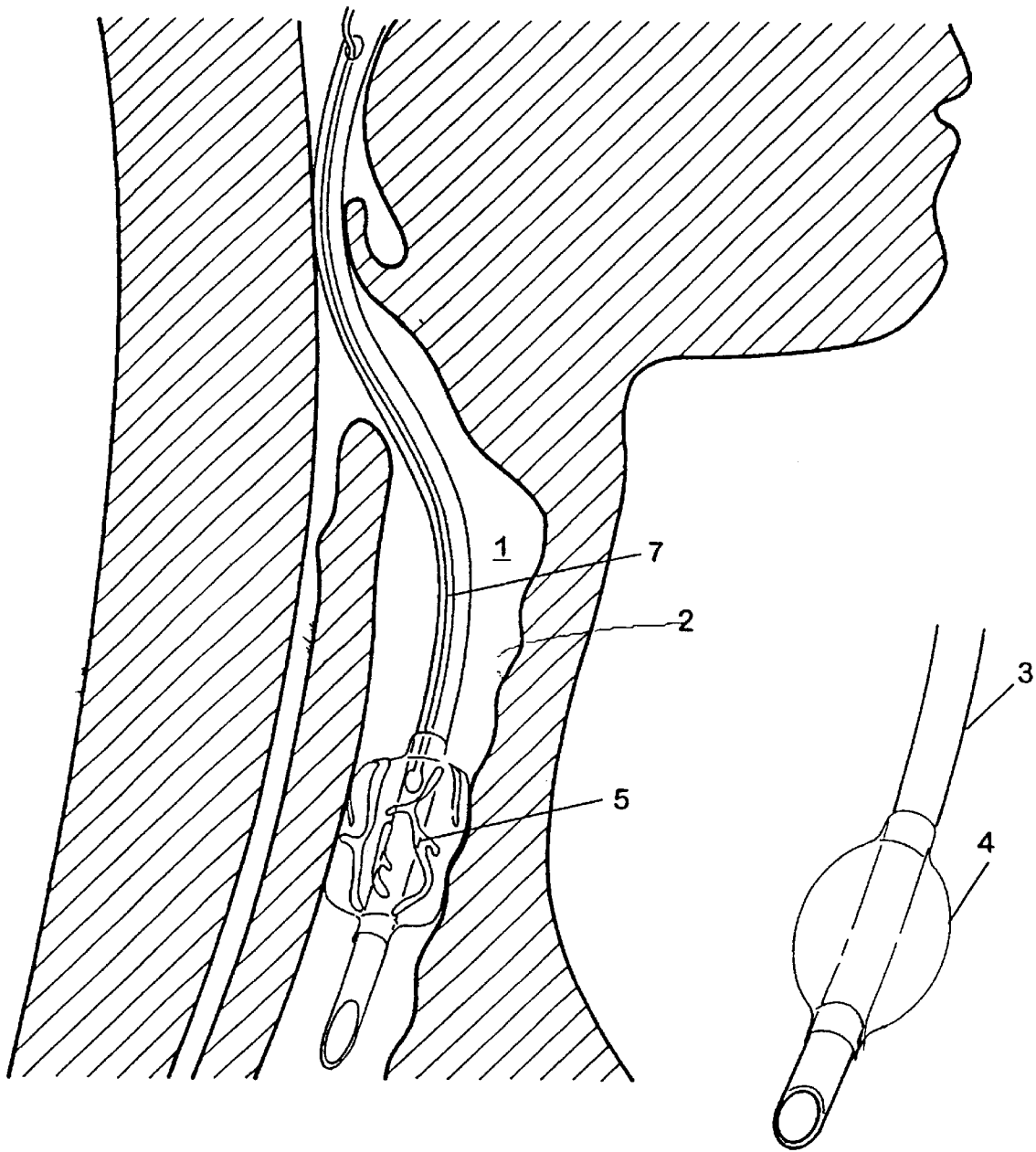

The present invention relates to a tracheal tube with an inflatable balloon, around the tube, the so called cuff which is in contact with the tracheal wall with the purpose of sealing the airway, and which is through a separate channel connected to the outside in order to monitor and regulate the pressure within the cuff. Such tracheal tubes are used for controlled ventilation of the lungs during anaesthesia and intensive care, during which he cuff seals up for respiratory air between the inside of the trachea and the tracheal tube. Apart from this, the cuff shall prevent liquid and secretions from entering the lungs. Additionally, it is important that the pressure of the cuff against the tracheal wall does not impede the blood supply to the tracheal mucosa. The best way to accomplish these functions is to use cuffs with a diameter larger than that of the trachea, because a homogeneous pressure on the tracheal wall is then achieved, as this pressure is regulated by the inside pressure in the cuff only. However, a high-volume cuff has certain drawbacks. The larger diameter of the cuff in relation to that of the trachea implies that the cuff has longitudinal folds when it is inflated inside the trachea, and these folds will create channels through which liquid and secretions with bacteria may get past the cuff and result in infection of the lungs.

From WO 95/09665 is known a tracheal tube comprising a cuff with a number of axially arranged ring-formed bulges providing a number of ring-formed contacts between the cuff and the trachea. From DE-A-35 19 626 (D2) is known a balloon catheter for the treatment of vessels, e.g. coronary vessels. The balloon is equipped with a distal portion comprising circumferential rings to help inflating the balloon.

The purpose of this invention is to design a tracheal tube which has the advantages of the known tracheal tubes, but prevents the disadvantage of forming channels between the trachea and the cuff. In accordance with the invention, this problem is solved with a tracheal tube as defined in claim 1.

More specifically, it is stated in claim 1 that the cuff has a number of local bulges distributed along the circumference of the balloon. In this way it is ensured that the channels, which are formed by the length-wise folds when the cuff is inflated inside the trachea, will be interrupted by areas with bulges. The thickness of the membrane in the bulges is reduced in comparison with the thickness of the membrane in the rest of the cuff. By this is ensured that the lengthwise folds which are formed, will be tightly closed by areas with bulges and that transport of liquid and secretions past the areas with local bulges is prevented.

By imparting to the bulges an elongate shape, as stated in claim 2, with the longitudinal axis in the direction of the circumference, it is furthermore ensured that the length-wise folds are interrupted by transverse bulges.

In another version according to claim 3, the bulges have an elongate shape with the longitudinal axis in an angled direction in relation to that of the circumference. As a result, the bulges become longer in the longitudinal direction, and transport of liquid in a length-wise fold is reduced, because a length-wise fold will pass a longer distance with thin-walled bulges, if the orientation of the bulges is angled compared to transversal.

By giving the balloon two or more rows of bulges, according to claim 4, the length-wise folds will be interrupted by one or more bulges, and the transport of liquid will be reduced.

It will be advantageous, as stated in claim 5, if the bulges in each row are staggered in relation to each other, so that any fold in the length-wise direction will be crossing a bulge.

In an advantageous version, according to claim 6, the bulges in two adjacent rows are placed with different angled directions of the longitudinal axis. By this, additional safety is obtained against uninterrupted folds with channels from the area above the cuff to the area below the cuff. As a result, any transport of liquid in a length-wise fold is reduced.

The channels that are formed when the bulges collapse against the inside of the tracheal wall must be very narrow in order to effectively prevent transport of fluid. Accordingly, the material of the bulges must be very soft and very thin-walled, and it has been proved that a good result is obtained with a wall-thickness of less than 30 micrometer. Because the areas with bulges are pressed against the tracheal wall, the reduced wall-thickness in the bulges will not reduce the ability of the cuff to resist pressure during the inflation.

Figures 2, 2A:
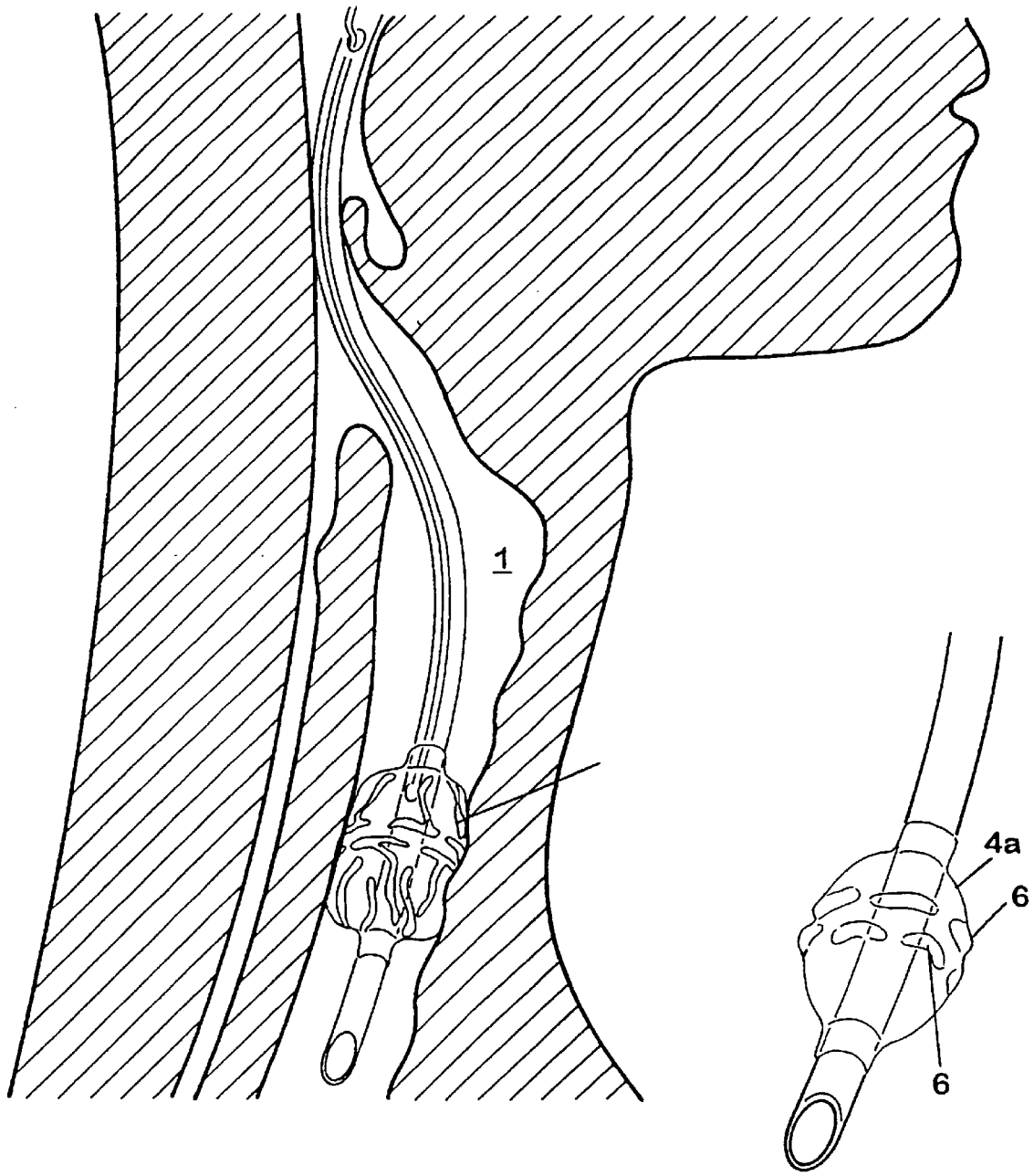

A detailed description of the invention is described in the following text with reference to the drawings, where FIG. 1 shows an example of a conventional tracheal tube, FIG. 1a shows the known catheter placed with the inflated cuff inside the trachea, FIG. 2 shows a sample of the catheter in accordance with the invention, FIG. 2a shows the catheter shown in FIG. 2 placed inside the trachea with the inflated cuff.

The known tracheal tube, which is shown in FIG. 1 with the cuff 4 in inflated state, consists of a tube 3 intended for intubation into the trachea, as shown in FIG. 1a. Through this tube the lungs can be ventilated, as the cuff blocks the passage of air between the tube 3 and the inside of the trachea 2.

A thin tube 7 connects the inside of the cuff with the surroundings and through this tube the inside pressure of the cuff may be accurately regulated. The cuff is inflated with atmospheric air and, as seen in FIG. 1, the cuff spreads over a certain length of the tube 3 and is permanently bonded to the tube at both its ends. At extubation, the cuff is emptied though the thin tube 7 and collapses around the tube 3, after which the tube can be removed. The cuff 4 has a larger diameter than the trachea itself 1 and when it is inflated inside the trachea, folds 5 will be formed, as shown in FIG. 1a. There will be length-wise channels in the folds 5, through which liquid and secretions may pass from the area above the cuff to the area below the cuff. Due to this, the known cuff involves a risk of infection of the patients lungs.

FIG. 2 shows a version of the tracheal tube in accordance with the invention, where the cuff 4a has a number of bulges 6 in the area which is in contact with the tracheal wall. As demonstrated in FIG. 2a, the bulges 6 will collapse when the cuff is inflated after the tube has been placed inside the trachea and simultaneously the length-wise folds will be interrupted by the area with bulges.

In the version shown in FIGS. 2 and 2a, the bulges are elongated with the longitudinal axis in the direction of the circumference and at the same time it has two rows of bulges which are staggered in the length-wise direction of the cuff. This version is advantageous, because it effectively prevents length-wise folds from passing through the area without being interrupted by bulges, and in this way uninterrupted channels from the area above the cuff to the area below the cuff is prevented. Meanwhile, the bulges may have any other shape or orientation and there may be more than two rows.

It is important that the wall of the cuff where the bulges are placed is flexible, so that the folds at this place do not form channels with a cross-section sufficient for passage of liquid or secretions containing infectious material. To achieve this, it is appropriate for cuffs manufactured from pvc that the wall-thickness in the areas with bulges is less than 30 micrometer.

What is claimed is:

1. A tracheal tube comprising a high-volume inflatable cuff surrounding the tube, said cuff adapted to be introduced into and seal against a trachea of a patient, the cuff being connected to surroundings of the patient through a separate channel in order to monitor and regulate pressure within the cuff in an inflated state, the cuff comprising an inflatable membrane formed with inflatable bulges distributed over that area of the cuff which when inflated is in contact with the trachea, wherein the bulges are spaced apart around a circumference of the cuff so as to be surrounded by membrane that does not include bulges, the bulges being collapsible when brought into contact with the trachea.

2. A tracheal tube according to claim 1, wherein the bulges have an elongate shape with a longitudinal axis aligned in a direction of the circumference of the cuff.

3. A tracheal tube according to claim 1, wherein the bulges have an elongate shape with a longitudinal axis of the elongate shape aligned at an angled direction compared to a direction of the circumference of the cuff.

4. A tracheal tube according to claim 2, wherein the bulges are placed in two or more rows, each row extending in a direction of the circumference of the cuff.

5. A tracheal tube according to claim 4, wherein each row is staggered in relation to an adjacent row in the direction of the circumference of the cuff, so that one bulge in a row is placed opposite an area of the membrane without any bulge in the adjacent row in a direction along an axis of the tracheal tube.

6. A tracheal tube according to claim 3, wherein the bulges in two adjacent rows are placed with the longitudinal axis of the cuff in different angled directions.

7. A tracheal tube according to claim 1, wherein a wall thickness of the cuff in the bulges is less than 30 micrometer.

* * * * *